United States Patent [19]
Highman et al.

[11] Patent Number: 5,700,365
[45] Date of Patent: Dec. 23, 1997

[54] CROSSLINKED POLYACRYLAMIDE GELS WITH HIGH MONOMER:CROSSLINKER RATIOS

[75] Inventors: Timothy J. Highman, North Royalton; Michael E. Smerdel, Shaker Hts.; Stephen M. Behm, Avon, all of Ohio

[73] Assignee: Amresco Inc., Solon, Ohio

[21] Appl. No.: 416,347

[22] Filed: Apr. 4, 1995

[51] Int. Cl.$^6$ .................................................. C25B 9/00
[52] U.S. Cl. .................. 204/469; 204/456; 204/470; 204/606; 436/161; 436/178
[58] Field of Search ..................... 204/299 R, 182.8, 204/456, 469, 470, 606; 436/161, 178

[56] References Cited

U.S. PATENT DOCUMENTS

| | | | |
|---|---|---|---|
| 4,950,708 | 8/1990 | Hochstrasser | 524/728 |
| 5,283,196 | 2/1994 | Hochstrasser et al. | 436/86 |

*Primary Examiner*—Howard E. Schain
*Assistant Examiner*—C. Delacroix-Muirheid
*Attorney, Agent, or Firm*—Foley & Lardner

[57] ABSTRACT

Improved polyacrylamide-type gels utilizing diacrylyl tertiary amide crosslinkers are disclosed having relatively high monomer:crosslinker ratios in comparison to conventional polyacrylamide gels. The resulting gels have pore structures chemically and physically different from conventional polyacrylamide gels and, when prepared in the optimal monomer:crosslinker ratio, provide superior resolution and structural characteristics over the conventional polyacrylamide gels.

14 Claims, 4 Drawing Sheets

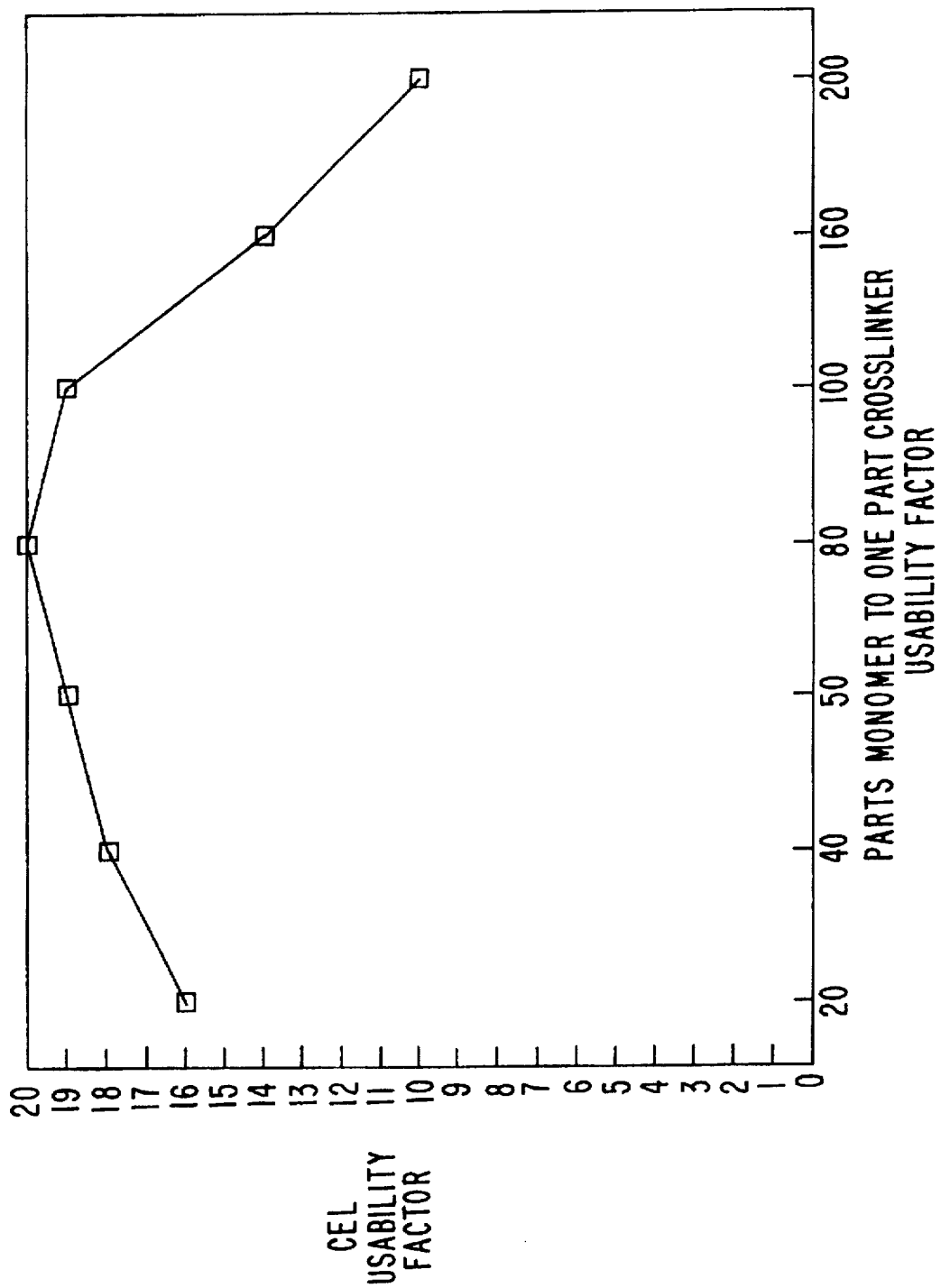

CROSSLINKED POLYACRYLAMIDE GELS WITH HIGH MONOMER: CROSSLINKER RATIOS

BACKGROUND OF THE INVENTION

Polyacrylamide electrophoresis has long been recognized as a powerful tool for resolving nucleic acid fragments, DNA sequencing products, proteins and polypeptides (Stellwagen, *Biochem.*, 22(1983): 6186; Hames et al., eds., *Gel Electrophoresis of Proteins*, Oxford University Press, New York 1981). Conventional polyacrylamide gels, however, have limitations as to resolving power for different ranges of molecular weight materials, the ability to adequately resolve low molecular weight fragments of similar sizes, and resolution of DNA sequencing products and gel strengths, especially with thin DNA-sequencing-type gels. An additional limitation has been high background staining levels with silver stains, which interferes with resolution.

Hochstrasser et al. (U.S. Pat. No. 5,283,196 and *Analytical Biochemistry*, 173(1988): 412-423) developed new cross-linkers, including diacrylylpiperazine, which helped to eliminate some of the background problems encountered with N,N'-methylenebisacrylamide, the conventional crosslinker used to prepare polyacrylamide gels. Hochstrasser et al. achieved slight improvements in gel strength and electrophoretic separations with the new crosslinkers, but the improvements were borderline at best.

The highest monomer:crosslinker ratio employed by Hochstrasser was 37.5:1 (or 30:0.8), as shown in column 7, line 68. The ratios used in Hochstrasser comport with the ratios used in conventional polyacrylamide gels, i.e., a range of about 19:1 to 37.5:1. Larger ratios are almost never used because the resulting gels are too weak for practical use and would provide poor resolution.

A second measurement, known as "acrylamide gel concentration", is the percentage of the amount by weight of monomer plus crosslinker that is used in the final gel relative to the total weight of all components in the gel. Typically, acrylamide gel concentrations of 4–20% are used, with concentrations of 6–12% being the more commonly used levels. Lower acrylamide gel concentrations generally are mechanically too weak, and higher concentrations limit electrophoretic mobility. The acrylamide gel concentrations used in Hochstrasser are within the conventional range.

It should be noted that Hochstrasser was concerned primarily with the silver-staining problem of conventional gels, and this is the problem that Hochstrasser solved with diacrylpiperazine. However, in the absence of the discovery described herein, there would have been no way to anticipate that outstanding resolution, gel strength and staining characteristics of diacrylyl tertiary amide-type cross-linkers could be obtained at unconventionally high monomer:crosslinker ratios. This finding is contrary to the teachings of the prior art.

SUMMARY OF THE INVENTION

Unexpectedly, the present inventor discovered that diacrylyl tertiary amides, especially diacrylylpiperazine, provide superior polyacrylamide gels (far better than suggested by Hochstrasser) when used at monomer:crosslinker ratios higher than the ratios conventionally used with polyacrylamide gels and those used by Hochstrasser. Because of their unique N-containing ring structure, these crosslinkers can yield comparable gel strengths to bis-acrylamide, but at lower concentrations. Further, because the crosslinker is used at lower concentrations, one can obtain larger pore sizes in the gel (at comparable total gel concentrations as used in conventional polyacrylamide gels), which results in improved resolution of molecules, even those similar in size and weight.

The present inventor further discovered that diacrylyl tertiary amide crosslinkers, when used at the high monomer:crosslinker ratios of the present invention, provide satisfactory gels even when the acrylamide gel concentration is below 4% and above 20%. It was found that satisfactory gels result from concentrations ranging from 3.0% to 25.0%. These advantages are neither taught nor suggested in Hochstrasser.

BRIEF DESCRIPTION OF THE DRAWINGS

FIG. 4 is a graph of monomer:crosslinker ratio (X-axis) versus gel usability (Y-axis), which demonstrates the improved usability of gels prepared according to the present invention.

DETAILED DESCRIPTION OF THE PREFERRED EMBODIMENTS

Figure 1:
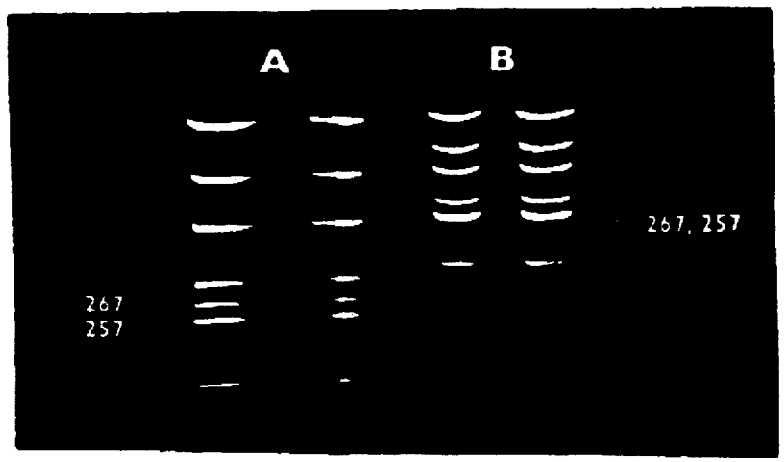
FIG. 1 is a comparison of the resolution of fragments of similar sizes between a gel of the present invention (A) and a conventional bis-acrylamide gel (B).

The present invention is directed to a composition for detecting and separating molecules comprising an improved polyacrylamide gel made from crosslinkers which are polymerizable amine acryloyl and methacryloyl derivatives of compounds having at least one secondary amine which forms a tertiary amide group, wherein the monomer:crosslinker ratio ranges from about 1:40 to about 1:480. The acrylamide gel concentration in the composition ranges from 3.0% to 25.0% by weight of the composition.

Another embodiment of the present invention is a method for detecting molecules comprising placing a sample containing molecules onto a composition comprising a gel which comprises an acrylamide monomer crosslinked with an amine acryloyl derivative of an amino compound having at least one secondary amine group, said derivative also having at least one tertiary amide group, wherein the ratio of acrylamide monomer:acryloyl derivative ranges from about 40:1 to about 480:1, and wherein the concentration of the gel in the composition is between 3.0% and 25.0% by weight of the composition, contacting the composition with a solvent for a sufficient length of time to cause the molecules to migrate differentially through the composition a predetermined distance, and contacting the composition with a silver solution to develop the composition and detect the relative positions of the molecules in the sample.

The crosslinkers may contain more than one acryloyl group or more than one tertiary amide group. In particular, diacrylyl tertiary amides, especially diacrylylpiperazine, are preferred crosslinkers. The crosslinkers are prepared as shown in U.S. Pat. No. 5,283,196 (Hochstrasser), which is incorporated herein by reference. The diacrylyl tertiary amide-type crosslinkers of the present invention are those of the following formulae:

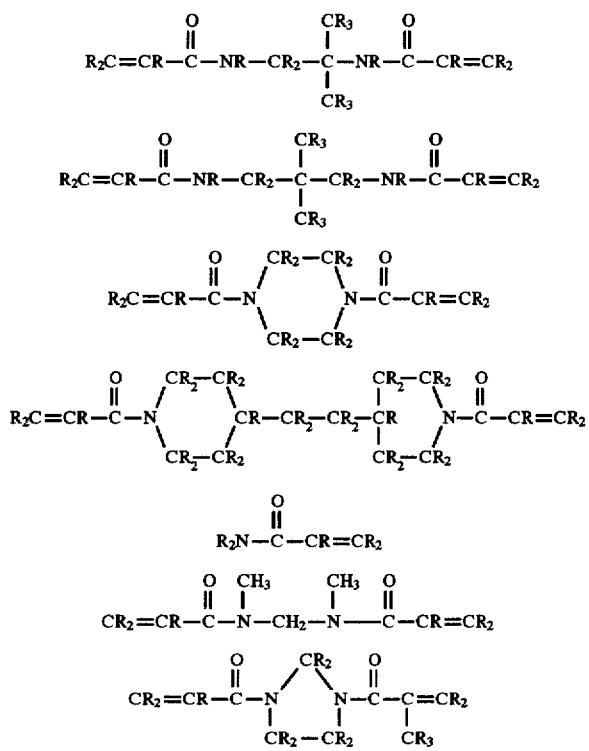

wherein each R group can be H, methyl, ethyl, propyl, isopropyl or butyl.

The crosslinked polyacrylamide gels are prepared according to standard techniques for preparing such gels using the crosslinkers described herein. For example, electrophoretic matrices are prepared from an aqueous solution of acrylamide type monomers of formula (II):

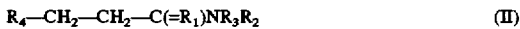

$R_4-CH_2-CH_2-C(=R_1)NR_3R_2$ (II)

wherein $R_1$ is O or S, and $R_2$, $R_3$, and $R_4$ independently represent hydrogen or a $C_1-C_5$ alkyl which is optionally substituted with at least one —OH group or with at least one =O group. These matrices may be prepared in buffered or unbuffered solutions according to standard gel preparation techniques known in the art. Such solutions may contain any combination of denaturants, including ionic, non ionic and zwitterionic detergents as well as other chelotropic agents or modifying agents commonly used to make crosslinked polyacrylamide gels.

The term "monomer:crosslinker ratio" refers to the amount by weight of monomer in the gel relative to the amount by weight of crosslinker in the gel. In the present invention, the monomer:crosslinker ratio ranges from about 40:1 to about 480:1. Preferably, the ratio ranges from about 50:1 to about 150:1. Still another preferred range is from about 101:1 to about 480:1.

The present inventor discovered through a wide-ranging series of tests that the diacrylyl tertiary amide-type of crosslinker provides superior levels of resolution and gel strength when used in the monomer:crosslinker ratio range of from 50:1 to 150:1. However, satisfactory results also were observed when the ratios were as small as 40:1 or as large as 480:1.

In an approximate sense, the observed effects can be likened to a "bell-shaped" response curve wherein a broad maximum effect was seen at a particular ratio range, followed by a decreased response as the ratio of monomer to crosslinker both increased and decreased from the broad optimum. The precise optimal ratio range varies depending upon the characteristics of the molecules being analyzed, the final acrylamide concentration, and the selected buffers, voltage, time and denaturing agents.

In retrospect, it is easy to see why some improvements in performance were seen by Hochstrasser in some instances, but not in others. The highest monomer:crosslinker ratio employed by Hochstrasser for the diacrylpiperazine crosslinker was 37.5:1 (or 30:0.8). Hence, Hochstrasser was at the trailing end of a bell-shaped response curve wherein the effects were minimal in comparison to the superior results seen at the relatively high ratios of the present invention. See FIG. 4. The less-than-optimal resolutions seen at ratios around 37.5:1 actually becomes even worse as the ratio decreases further within the conventional range of ratios (first at a ratio of 29:1 and later at a ratio of 19:1). See FIG. 4.

The present invention is further illustrated by, though in no way limited to, the following examples.

Example 1

A 40% stock solution was prepared containing 39.5 g of ultra pure acrylamide and 0.5 g of diacrylpiperazine in 1000 ml of deionized water. The 40% stock solution was diluted to 20% and buffered in 1× Tris/Borate/EDTA (0.089M Tris, 0.089M Borate and 0.002M EDTA). The resulting solution was subjected to vacuum pressure (100–500 torr) for 5 minutes to remove dissolved gases that could inhibit polymerization. To initiate polymerization, 1 ml of 10% ammonium persulfate and 100 µl N,N,N',N'-tetramethylethylenediamide (TEMED) was added to 100 ml of diluted gel solution and the gel was cast between two glass plates separated by 0.8 mm spacers and allowed to polymerize at room temperature for 1 hour. Nucleic acid molecular weight standard was prepared for electrophoresis by diluting to a final concentration of 100 µg/ml in a standard loading buffer. The molecular weight standard consisted of double stranded DNA fragments of the following base pair sizes: 587, 458, 434, 298, 267, 257 and 174. Ten microliters (1 µg of DNA) was applied to two gels of differing makeup. To exemplify the difference between the matrix described above and conventional polyacrylamide gels, the samples were subjected to electrophoresis in gels crosslinked with diacrylyl tertiary diamide-type cross linkers and conventional bis-acrylamide crosslinked gels. Both gel systems were buffered with 1× TBE.

Following electrophoresis, the gel plates were disassembled and the gels were stained for 30 minutes in 1 mg/ml ethidium bromide in distilled deionized water. Gels were then destained for 30 minutes in distilled deionized water before being photographed with a FCR-10 camera. Results are presented in FIG. 1. As can clearly be seen, the gels in column A, the diacrylyl tertiary diamide crosslinked gels, provided superior resolution of fragments of similar size (267 bp and 257 bp), while the gels in column B, the bis-acrylamide crosslinked gels, failed to adequately resolve these fragments. Resolution is defined here as the ability to resolve the components into single defined regions, clearly separated and distinguishable from proximate molecules. The gels of column A also exhibited superior resiliency and resistance to breakage when compared to those of column B.

Example 2

A 40% stock solution was prepared containing 39.5 g of ultra pure acrylamide and 0.5 g of diacrylylpiperazine in 1000 ml of deionized water. The stock solution was diluted to 6% in 1× Tris/Borate/EDTA (0.089M Tris, 0.089M Borate and 0.002M EDTA) and urea was added to a final concentration of 7.0M. To this solution, a vacuum was applied for five minutes and then 1 ml of 10% ammonium persulfate and 100 µl of TEMED was added to initiate polymerization.

The resulting solution was cast between two glass plates with 0.4 mm spacers and allowed to polymerize at room temperature for 1 hour. DNA sequencing reactions were prepared according to Sanger dideoxy sequencing methods using a modified T7 polymerase and α-$^{32}$P-dATP. To exemplify the difference between the matrix described above and conventional polyacrylamide gels, the samples were subjected to electrophoresis in gels crosslinked with diacrylyl tertiary diamide-type crosslinkers and bis-acrylamide crosslinked gels. Both gel systems were buffered with 1× TBE.

Figure 2A:
FIG. 2 is a comparison of the electrophoresis band patterns resulting from DNA sequencing using a gel of the present invention (A) and a conventional bis-acrylamide gel (B).
Figure 2B:

DNA sequencing products were visualized by autoradiography. As can clearly be seen in FIG. 2, the gel in column A, the diacrylyl tertiary diamide crosslinked gels, provided an increase in the number of readable bases when compared to the gel in column B, the bisacrylamide crosslinked gels. Gels crosslinked with diacrylyl tertiary diamide crosslinkers displayed banding patterns that provided a larger number of resolved bands in a given migration area. Resolution is defined here as the ability to resolve the components into single defined regions, clearly separated and distinguishable from proximate molecules. The gels seen in column A also exhibited superior resiliency and resistance to breakage when compared to those in column B.

Example 3

A 40% stock solution was prepared containing 39.5 g of ultra pure acrylamide and 0.5 g of diacrylylpiperazine in 1000 ml of deionized water. The stock solution was diluted to 12% in 1× Tris/Glycine/SDS (TG-SDS: 0.25M Tris base, 0.192M Glycine, 0.1% Sodium Dodecyl Sulfate). To this solution, a vacuum was applied for five minutes and then 1 ml of 10% ammonium persulfate and 100 µl of TEMED was added to initiate polymerization.

Figure 3:
FIG. 3 shows the electrophoresis band pattern resulting from protein molecular weight standards using a gel of the present invention.

The resulting solution was cast between two glass plates with 1.0 mm spacers and allowed to polymerize at room temperature for 1 hour. Protein molecular weight standards (14 kD–66 kD) were subjected to electrophoresis in the afore-mentioned matrix buffered with 1× TG-SDS. Following electrophoresis, the gel was fixed in acetic acid, then stained with silver nitrate and developed with a sodium bicarbonate/sodium thiosulfate solution. The results are displayed in FIG. 3.

Gels prepared with diacrylyl tertiary amide-type cross linkers display less background when subjected to silver staining. In addition, the glycine front (characteristic of bis-acrylamide crosslinked gels) was absent in the gels crosslinked with diacrylyl tertiary amide-type cross linkers.

Example 4

Concentrated stock solutions were prepared at varying monomer:crosslinker ratios ranging from 19:1 to 37.5:1 (the conventional range of monomer:crosslinker ratios) up through 60:1, 75:1 and finally, 150:1. Resolution was characterized by subjecting nucleic acid size markers to electrophoresis in the different matrices. It was found that, as the ratio of monomer:cross linker increased, resolution improved to an optimum point at 75:1.

Gels prepared at a monomer:crosslinker ratio of 19:1 and 37.5:1 provided resolution that (for practical purposes) was unacceptable. Band formation was not precise and fragments of similar size were not distinctly resolved. As the ratio of monomer: crosslinker increased, however, a marked improvement was noted in the resolution and band formation of the nucleic acid fragments. As shown in FIG. 4, an optimum was reached at a monomer:crosslinker ratio range between 75:1 and 150:1. At ratios beyond these, gel strength and manageability was compromised. At ratios above 150:1, it remained possible to polymerize the gels, but curing times and the ability to effectively manipulate the gel were less desirable.

While the invention has been described in detail and with reference to specific embodiments thereof, it will be apparent to one skilled in the art that various changes and modifications can be made therein without departing from the spirit and scope of the invention.

What is claimed is:

1. A composition for separating and detecting molecules comprising a gel which comprises an acrylamide monomer crosslinked with an amine acryloyl derivative of an amino compound having at least one secondary amine group, said derivative also having at least one tertiary amide group, wherein the ratio of acrylamide monomer:acryloyl derivative ranges from 40:1 to about 150:1, and wherein the concentration of the gel in the composition is between 3.0% and 25.0% by weight of the composition.

2. The composition as claimed in claim 1 wherein the ratio of acrylamide monomer:acryloyl derivative ranges from about 50:1 to about 150:1.

3. The composition as claimed in claim 1 wherein the concentration of the gel in the composition is between 3.0 and 15.0%.

4. The composition as claimed in claim 1 wherein the acrylamide monomer is a compound of formula (II):

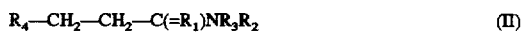

$$R_4-CH_2-CH_2-C(=R_1)NR_3R_2 \quad (II)$$

wherein $R_1$ is O or S, and $R_2$, $R_3$, and $R_4$ independently represent hydrogen or a $C_1$–$C_5$ alkyl which is optionally substituted with at least one —OH group or with at least one =O group.

5. The composition as claimed in claim 1 wherein the acryloyl derivative is a compound of one of the following formulae:

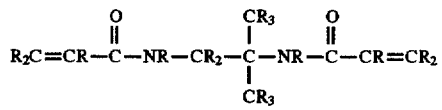

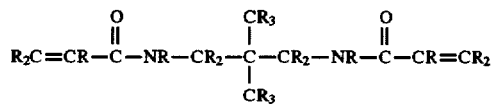

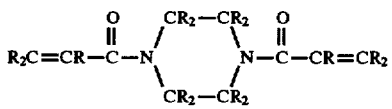

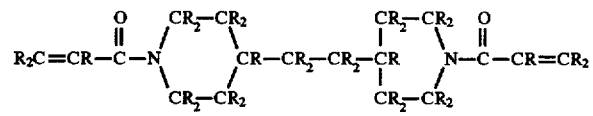

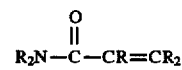

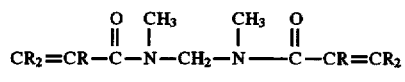

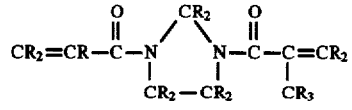

wherein each R group can be H, methyl, ethyl, propyl, isopropyl or butyl.

6. The composition as claimed in claim 5 wherein the acryloyl derivative is diacrylpiperazine.

7. A method for detecting molecules comprising placing a sample containing molecules onto a composition comprising a gel which comprises an acrylamide monomer crosslinked with an amine acryloyl derivative of an amino compound having at least one secondary amine group, said derivative also having at least one tertiary amide group, wherein the ratio of acrylamide monomer:acryloyl derivative ranges from 40:1 to about 150:1, and wherein the concentration of the gel in the composition is between 3.0% and 25.0% by weight of the composition, contacting the composition with a solvent for a sufficient length of time to cause the molecules to migrate differentially through the composition a predetermined distance, and contacting the composition with a silver solution to develop the composition and detect the relative positions of the molecules in the sample.

8. The method as claimed in claim 7 wherein the ratio of acrylamide monomer:acryloyl derivative ranges from about 50:1 to about 150:1.

9. The method as claimed in claim 7 wherein the concentration of the gel in the composition is between 3.0% and 15.0%.

10. The method as claimed in claim 7 wherein the acrylamide monomer is a compound of formula (II):

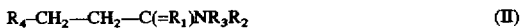

(II)

wherein $R_1$ is O or S, and $R_2$, $R_3$, and $R_4$ independently represent hydrogen or a $C_1-C_5$ alkyl which is optionally substituted with at least one —OH group or with at least one =O group.

11. The method as claimed in claim 7 wherein the acryloyl derivative is a compound of one of the following formulae:

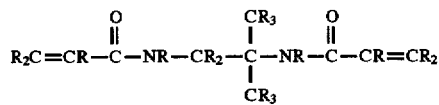

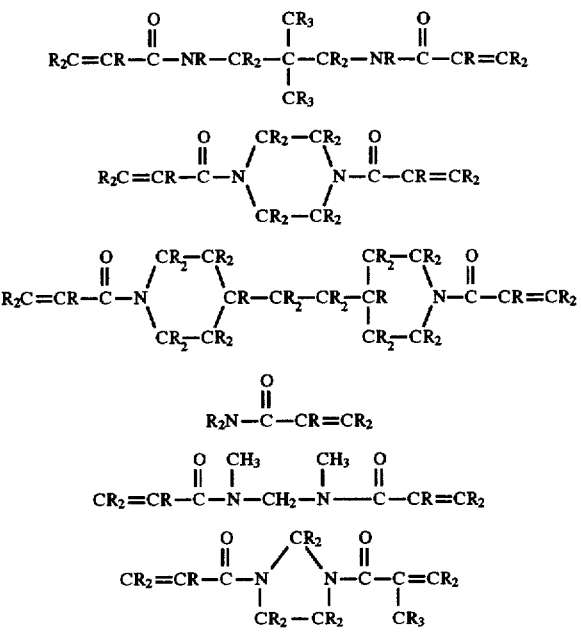

wherein each R group can be H, methyl, ethyl, propyl, isopropyl or butyl.

12. The method as claimed in claim 11 wherein the acryloyl derivative is diacrylpiperazine.

13. The composition as claimed in claim 1 wherein the ratio of acrylamide monomer:acryloyl derivative ranges from 40:1 to about 100:1.

14. The method as claimed in claim 7 wherein the ratio of acrylamide monomer:acryloyl derivative ranges from 40:1 to about 100:1.

* * * * *